US008212027B1

(12) United States Patent
Woo et al.

(10) Patent No.: US 8,212,027 B1
(45) Date of Patent: Jul. 3, 2012

(54) PROCESS FOR THE CONVERSION OF CYCLIC AMINES INTO LACTAMS

(75) Inventors: Lee Keith Woo, Ames, IA (US); Robert J. Angelici, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 13/095,523

(22) Filed: Apr. 27, 2011

Related U.S. Application Data

(60) Provisional application No. 61/356,788, filed on Jun. 21, 2010.

(51) Int. Cl.
C07D 201/00 (2006.01)
C07D 213/63 (2006.01)
C07D 207/00 (2006.01)
(52) U.S. Cl. .................... 540/532; 546/291; 548/541
(58) Field of Classification Search .......... 540/532; 546/291; 548/541
See application file for complete search history.

(56) References Cited

U.S. PATENT DOCUMENTS 3,634,346 A * 1/1972 McKeon et al. ............. 540/532
3,745,164 A 7/1973 Adamek

OTHER PUBLICATIONS

Dahlhoff, Gerd, et al., "ϵ-Caprolactam: New By-Product Free Synthesis Routes", Catalysis Reviews, 43(4), pp. 381-441 (2001).
Shen, Hong C., "Recent advances in syntheses of heterocycles and carbocycles via homogeneous gold catalysis. Part 1: Heteroatom addition and hydroarylation reactions of alkynes, allenes, and alkenes", Elsevier, Tetrahedron 64 (2008), pp. 3885-3903.
Thomas, John Meurig, et al., "Design of a "green" one-step catalytic production of ϵ-caprolactam (precursor of nylon-6)", PNAS, vol. 102, No. 39, pp. 13732-13736, Sep. 27, 2005.
Zhu, Bolin, et al., "Aerobic oxidation of amines to imines catalyzed by bulk gold powder and by alumina-supported gold", Elsevier, Journal of Catalysis 260 (2008) pp. 1-6.

* cited by examiner

*Primary Examiner* — Bruck Kifle
(74) *Attorney, Agent, or Firm* — McKee, Voorhees & Sease, P.L.C.

(57) ABSTRACT

Converting cyclic amines to lactams using gold supported catalysts.

9 Claims, No Drawings

PROCESS FOR THE CONVERSION OF CYCLIC AMINES INTO LACTAMS

CROSS-REFERENCE TO RELATED APPLICATIONS

This application claims priority under 35 U.S.C. §119 of a provisional application Ser. No. 61/356,788 filed Jun. 21, 2010, and which application is hereby incorporated by reference in its entirety.

GRANT REFERENCE

This invention was made with government support under Contract No. DE-AC02-07CH11358 awarded by DOE. The government has certain rights in the invention.

BACKGROUND OF THE INVENTION

Caprolactam is the popular monomer for the versatile nylon-6 polyamide, which offers excellent properties like a high strength-to-weight ratio, good chemical and thermal stability, and durability. Textile yarn manufactured from nylon-6 exhibits fine drape, resistance to abrasion, high flexibility, chemical and biological stability, etc. Nylon-6 is widely used in the manufacture of fishing nets, tire yarns, sewing threads, industrial drive belts, etc. As an engineering plastic, it has found a wide application in castings, injection molding, and extrusion. Products manufactured using nylon-6 offer excellent engineering properties, even at high temperatures. The precursor to nylon-6 caprolactam is sold internationally on a very large scale (several billion pounds annually). A competitive and environmentally friendly process of making ε-caprolactam would be extremely desirable.

The ever increasing industrial demand for nylon-6 (polycaprolactam) necessitates the development of environmentally benign methods of producing its precursor, ε-caprolactam. The precursor to nylon-6, ε-caprolactam, is currently manufactured on a massive scale through two favored methods, each of which starts from cyclohexanone. In one, the oxidant that forms the intermediate cyclohexanone oxime is hydroxylamine sulfate, and ammonia is used to neutralize the liberated acid. In the other, a far less environmentally aggressive oxidant, aqueous $H_2O_2$ is used in conjunction with a solid redox catalyst, a titanosilicate known as TS-1, to ammoximize the ketone. However, both methods entail the use of oleum to effect the Beckmann rearrangement of the oxime to the lactam and the former method generates very large quantities of low-value ammonium sulfate as by-product.

The avoidance of production of large amounts of low value and unwanted ammonium sulfate would be desirable. So too would it be desirable for production of ε-caprolactam by a method which avoids any use of the highly corrosive fuming sulfuric acid.

It also goes without saying that the process must also have a commercially satisfactory yield level. Current processes approximate about 60% yield for conversion of cyclohexanone to ε-caprolactam. Thus a successful competitive, environmentally friendly process must approximate these yields.

It is a primary objective of the present invention to develop an environmentally friendly (green) one-step catalytic production of ε-caprolactam (precursor of nylon-6) which avoids generation of large quantities of low-value ammonium sulfate as a byproduct, and which avoids use of fuming sulfuric acid, a highly corrosive difficult-to-handle material.

It is a further objective of the present invention to develop such a process which provides conversion of cyclic amines to lactams at competitive yield levels.

The method and means of accomplishing each of the above objectives will become apparent from the detailed description of the invention which follows hereinafter.

BRIEF SUMMARY OF THE INVENTION

Cyclic amines are treated with oxygen in a moderate polarity to non-polar solvent such as toluene to give lactams, all in the presence of a gold/silicon dioxide catalyst at yields of 50% or higher. The reaction is preferably conducted in the presence of excess oxygen, and can be accomplished at atmospheric pressure.

DETAILED DESCRIPTION OF THE PREFERRED EMBODIMENTS

Lactams according to this invention may be prepared from the corresponding cyclic amines according to the following equation:

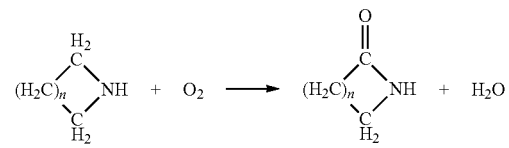

The letter "n" may be a whole number of from 1-6 but is preferably 3, 4 or 5 and most preferably n is 4 which corresponds to the lactam being ε-caprolactam, the monomer for Nylon-6. For the lactam product 2-piperidone n is three and where n is two the lactam product is 2-pyrrolidone, a precursor to the solvent N-methylpyrrolidone.

The reaction can be conducted suitably at atmospheric pressure or above. It is preferably conducted in the presence of excess oxygen. Reaction temperature can range from about 60° C. to about 150° C. It is preferably about 70° C. to 100° C.

The reaction is also conducted preferably in the presence of an organic solvent, and most preferably in the presence of a medium polar to nonpolar organic solvent, selected from the group consisting of toluene, tetrahydrofuran, acetonitrile, and other aromatic and nitrile solvents.

Best yields are obtained when the reaction is run in the presence of gold/silicon dioxide supported catalyst. The experiments indicate and demonstrate that the gold and the silicon dioxide need not be closely associated, that is, they can function separately if one wishes. The gold catalyzes one part of the reaction while the silicon dioxide catalyzes a second part as illustrated and discussed in Example 1. It is possible that other acids may catalyze the second reaction part. Pressure does not seem to play an important role in the reaction and it may be conducted at atmospheric pressure or super atmospheric pressure if desired.

Lactams may be isolated from the reaction product by standard techniques, in particular, distillation and crystallization. The gold catalyst is preferably finely divided. It may be possible to run the reaction without gold catalyst and other catalyst systems which avoids gold and its expense might be worthy of exploration. The amount of catalyst is from about 2 mole % to about 10 mole %.

The following examples are offered to further illustrate but not limit the above described invention.

Example 1

In Example 1, the starting cyclic amine material is piperidine (n equals 3). The reaction was run in the presence of 2-3 nm gold supported on silica dioxide (Cabosil) (2.5 wt % gold) obtained from Oak Ridge National Laboratories. The amount of gold catalyst supported on silica was 82 mg; the amount of piperidine was 0.2 mmol; used as a solvent was 5 mL of toluene. The gold catalyst and piperidine in the toluene were stirred and heated under an oxygen atmosphere to approximately 100° C.

During the course of the reaction, the amidine product appeared first, then 2-piperidone (valerolactam) began to form. The identity and yields of these compounds were determined by GC. Typically the reactions were run for 100 h. The yield of 2-piperidone under these conditions was approximately 60%, but it has not been optimized.

The initial appearance of the amidine followed by its disappearance suggests that the overall conversion of piperidine to 2-piperidone proceeds (valerolactam) by a two-step pathway represented by the following equation:

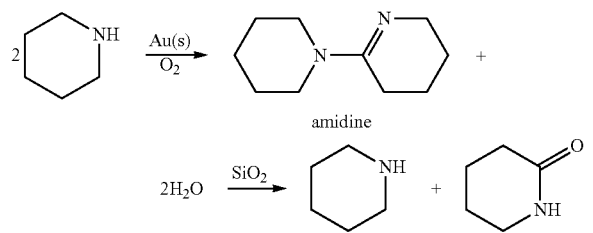

Example 2

In Example 2 a reaction identical to that of Example 1 was run except that the starting cyclic amine was the species where n=2 which results in the lactam product being 2-pyrrolidone (butyrolactam). Gas chromatography confirmed the resulting product as 2-pyrrolidone.

From the above examples it can be seen that the invention accomplishes at least all of its stated objectives.

What is claimed is:

1. A process of converting cyclic amines to lactams, comprising:
reacting a cyclic amine of the formula:

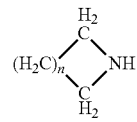

wherein n is from 2-4;
with oxygen in the presence of catalytically effective amount of a gold, silica supported catalyst, in a medium polar to non-polar organic solvent to provide a lactam of the formula:

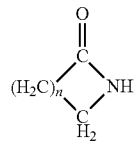

wherein n is from 2-4.

2. The process of claim 1 wherein the reaction is conducted in the presence Of excess oxygen.

3. The reaction of claim 1 wherein the reaction is conducted at temperatures from about 60° C. to about 150° C.

4. The process of claim 1 wherein the medium polar to non-polar organic solvent is selected from the group consisting of toluene, tetrahydrofuran acetonitrile, and other aromatic and nitrile solvents.

5. The process of claim 1 wherein n is 2, and the lactam product is 2-pyrrolidone.

6. The process of claim 1 wherein n is 3, and the lactam product is valerolactam.

7. The process of claim 1 wherein n is 4, and the lactam product is ε-caprolactam.

8. The process of claim 1 wherein the amount of catalyst is from about 2 mole % to about 10 mole %.

9. The process of claim 1 wherein the gold catalyst is used in conjunction with an acid.

* * * * *